United States Patent [19]

Chmiel et al.

[11] 4,382,913
[45] May 10, 1983

[54] PROCESS AND AN AGENT FOR THE ADSORPTION AND CATALYTIC DECOMPOSITION OF FOUL-SMELLING INTESTINAL GASES

[75] Inventors: Horst Chmiel, Leonberg; Günter Hellwig, Stuttgart, both of Fed. Rep. of Germany

[73] Assignee: Fraunhofer-Gesellschaft zur Forderung der angewandten, Munich, Fed. Rep. of Germany

[21] Appl. No.: 248,413

[22] Filed: Mar. 27, 1981

[30] Foreign Application Priority Data

Apr. 3, 1980 [DE] Fed. Rep. of Germany ....... 3013255

[51] Int. Cl.$^3$ ............................................. B01D 53/36
[52] U.S. Cl. ................................... 423/230; 423/231; 423/244; 423/245; 252/447; 604/333
[58] Field of Search .................... 423/230, 244 R, 245, 423/231; 55/73, 74; 128/283

[56] References Cited

U.S. PATENT DOCUMENTS

| | | | |
|---|---|---|---|
| 3,416,293 | 12/1968 | Alexander | 55/73 |
| 3,471,545 | 10/1969 | Giordano et al. | 252/454 X |
| 3,890,245 | 6/1975 | Berg et al. | 252/447 |
| 4,058,483 | 11/1977 | Henbest | 252/447 X |

*Primary Examiner*—Earl C. Thomas
*Attorney, Agent, or Firm*—Burns, Doane, Swecker & Mathis

[57] ABSTRACT

There is provided a process for the adsorption and catalytic decomposition of foul-smelling intestinal gases, particularly mercaptans, wherein the intestinal gases are passed through a highly specific adsorbent which, out of a mixture of water vapour, methanol, carbon monoxide and carbon dioxide and various sulfur-containing gases, particularly mercaptan-containing gases, catalytically decomposes and adsorbs only the sulfur and mercaptan compounds and optionally desorbs the non-smelling fractions. An absorbent for use in the method is characterized in that it contains an inert, highly porous solid having a specific surface according to BET of from 900 to 1800 m$^2$/g or pyrogenic silicon dioxide having a surface of from 50 to 500 m$^2$/g, the specific surfaces having been determined by argon adsorption at $-196°$ C., which are covered over their surface with from 0.1 to 5% by weight of aluminium, zinc, chromium or iron, based on the weight of the solid having a specific surface of 1000 m$^2$/g, or a mixture of metal-coated, inert highly-porous solids of this type.

6 Claims, 2 Drawing Figures

BREAKTHROUGH CURVE OF THE UNTREATED DRY CARBON

PROCESS AND AN AGENT FOR THE ADSORPTION AND CATALYTIC DECOMPOSITION OF FOUL-SMELLING INTESTINAL GASES

This invention relates to a process for the adsorption and decomposition of foul-smelling intestinal gases and to an agent for carrying out this process.

An artificial anus or *Anus praeternaturalis* often has to be fitted for the treatment of certain, occasionally malignant intestinal illnesses. Due to an increase in the incidence of intestinal cancer, the number of people wearing an *Anus praeternaturalis* is continuously increasing.

One of the difficulties of having to wear an *Anus praeternaturalis* lies in the fact that the stool and intestinal gases can no longer be voluntarily held back. The stool is caught in a truss pad provided with rubber rings, by which it is firmly applied to the body, or in an adhesively applied plastic bag. After acclimatisation, wearers of an *Anus praeternaturalis* are able to lead a normal social life.

One of the difficulties of having to wear a plastic bag lies in the removal of the intestinal gases which occur. The intestinal gases are the gaseous contents of the intestine and consist partly of inhaled air. Some are formed by reactions in the intestine. The carbohydrates and proteins which are left unaffected by the digestion processes in the upper parts of the intestine are bacterially degraded, primarily in the colon, into gaseous products which, although having a high energy content, can no longer be made useful to the organism. Products such as these include hydrogen, hydrogen sulfides, mercaptans, hydrocarbons (methane), carbon dioxide. The composition of the intestinal gases depends upon the nature of the diet, although foul-smelling substances are almost always present in the intestinal gases.

Thus, foul-smelling thiols, particularly methane thiol, are formed during the digestion process in the bacterial decomposition of proteins in the human stomach/intestine region. The odour threshold for the human nose is at 0.002 ppb (part per billion) for methane thiol ($CH_3SH$), i.e. even 2 parts of $CH_3SH$ are sufficient to release a noticeably unpleasant odour per $10^{12}$ parts of neutral gas. In the case of colostomy patients, intestinal gases containing methane thiol are given off uncontrollably, resulting in a particularly foul smell. The intestinal gas is a mixture of predominantly methane, $CO_2$, sulfur-containing hydrocarbon compounds (for example $CS_2$, $CH_3COSH$), such as thiols, in a substantially 100% saturated water vapour atmosphere.

The release of the foul-smelling gases is particularly unpleasant to the wearer of the Anus praeter because he must permanently have the feeling that he "smells". Attempts have been made in the past to remove the odours by placing carbon filters around the openings of the bags. However, these filters are attended by the disadvantage that the carbon becomes covered very quickly. The carbon adsorbs not only the foul-smelling substances, which predominantly contain sulfur products, particularly mercaptans, but also water vapour, carbon monoxide and carbon dioxide which are present in relatively large quantities in the intestinal gases. As a result, the carbon becomes "covered" very quickly and also loses its adsorption capacity for the foul-smelling substances. In addition, the surface of the adsorbent is rapidly poisoned by the sulfur compounds which occur.

This means that the filters have to be changed at very frequent intervals or that their adsorption capacity diminishes drastically with time and is only briefly maintained, i.e. for between a few minutes and 1 to 2 hours, depending on the amount of adsorbent.

Accordingly, there is a great need for substances which selectively adsorb only the foul-smelling constituents of intestinal gases but which do not adsorb non-smelling constituents such as methane, hydrogen and water vapour, carbon monoxide and carbon dioxide.

SUMMARY OF THE INVENTION

The object of the present invention is to provide a process and an agent for the adsorption and catalytic decomposition of foul-smelling intestinal gases both inside and outside the intestine. The process and the agent are intended to be effective for as long as possible, guaranteeing adsorption of the foul-smelling intestinal gases for a period of at least 12 hours.

In addition, the quantity of adsorbent per patient is intended to be kept as small as possible, in addition to which all the foul-smelling and toxic substances occurring in the intestinal gas are intended to be removed or rendered harmless.

The present invention relates to a process for the adsorption and catalytic decomposition of foul-smelling intestinal gases, particularly mercaptans, which is characterised in that the intestinal gases are passed through a highly specific adsorbent which, out of a mixture of water vapour, methanol, carbon monoxide and carbon dioxide and various sulfur-containing gases, particularly mercaptan-containing gases, catalytically decomposes and adsorbs only the sulfur and mercaptan compounds and optionally desorbs the non-smelling fractions.

The invention also relates to a highly specific adsorbent for carrying out the above process which is characterised in that it contains an inert, highly porous solid having a specific surface according to BET of from 900 to 1800 $m^2/g$ or pyrogenic silicon dioxide having a surface of from 50 to 500 $m^2/g$, the specific surfaces having been determined by argon adsorption at $-196°$ C., which are covered over their surface with from 0.1 to 5% by weight of aluminium, zinc, chromium or iron, based on the weight of the solid having a specific surface of 1000 $m^2/g$, or a mixture of metal-coated, inert highly porous solids of this type.

It has surprisingly been found that the adsorption capacity of certain inert, highly porous solids in the adsorption of the foul-smelling constituents of intestinal gases can be significantly improved by covering the surface of the highly porous solids with selected metals. Modification of the surface of the highly porous solids with metals increases the adsorption capacity for thiols and also the amount of thiol adsorbed.

DETAILED DESCRIPTION OF THE INVENTION

Figure 1:
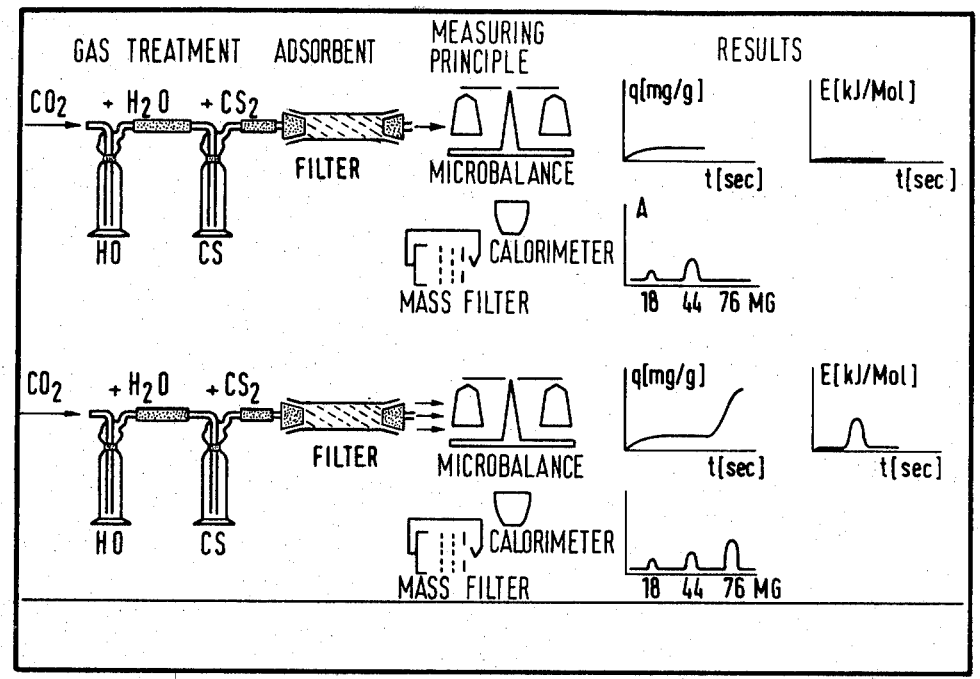
FIG. 1 diagramatically illustrates the construction of the measuring apparatus for a gas mixture of $CO_2$, $H_2O$ and $CS_2$ or $CH_2SH$, $C_2H_5SH$ and $CH_3COSH$.
Figure 2:
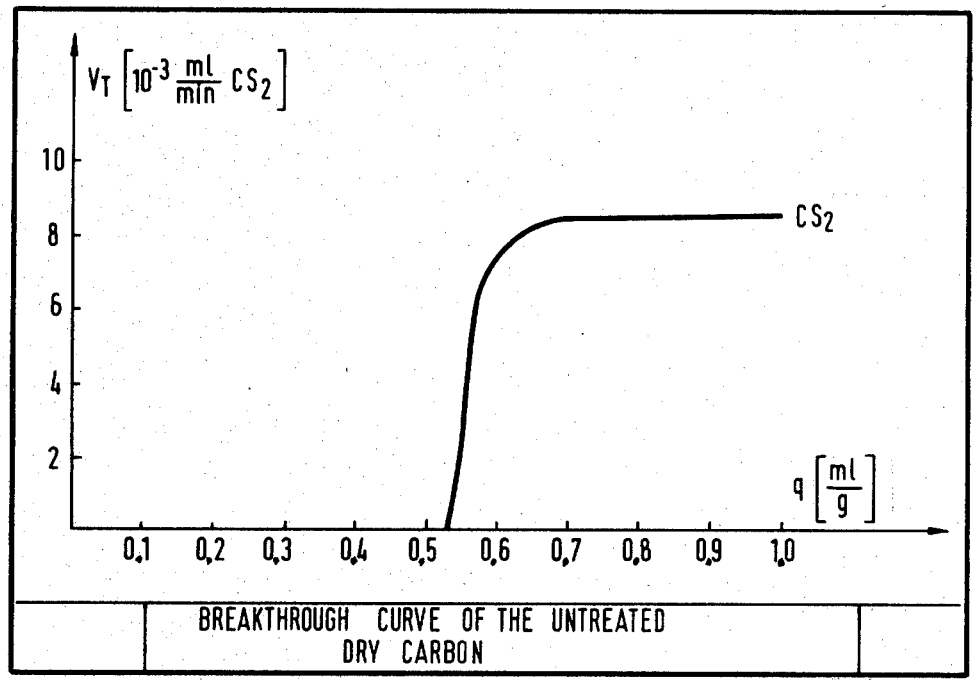
FIG. 2 is a graph illustrating the breakthrough curve for $CS_2$ of untreated dry carbon.

The highly specific adsorbents used in the process according to the invention are introduced into the colostomy bag, for example in filter cartridges, and it has surprisingly been found that, in general, from 0.5 to 3 g of adsorbent is sufficient to guarantee a 12 to 24 hour effective life of the filter in the colostomy patient. In addition, all the foul-smelling and toxic substances occurring in the intestine are removed or rendered harmless in the process according to the invention in conjunction with the agent according to the invention. Furthermore, the adsorption surface is not poisoned by the sulfur compounds occurring and retains its effect for a prolonged period, as mentioned above.

A highly specific adsorbent, of which the surface is modified under control, is used in accordance with the invention. The adsorbent used in accordance with the invention has to be an inert, highly porous solid, i.e. a solid which has a large specific surface and a pore distribution which ranges from micropores via mesopores to macropores. The solid may be present in various particle size ranges. For example, it may be a powder or may be present in the form of cylindrical or spherical elements. The particle sizes of the solid are generally in the range from 0.1 to 3 mm and preferably in the range from 0.2 to 0.5 mm.

Highly porous solids which may be used in accordance with the invention are, for example, active carbon, zeolites, metal oxides, such as for example aluminium oxide and silicon dioxide. Of these, the silicon dioxide may be used in the form of a gel or in the form of pyrogenic, non-porous silicon dioxide.

In addition, the porous solid used in accordance with the invention, namely the active carbon, the zeolites, the metal oxides, such as aluminium oxide or silicon dioxide, are required to have a large specific surface according to BET of from 900 to 1800 m²/g and preferably from 1000 to 1800 m²/kg. The larger the surface and the larger the number of adsorption centres having a predominantly polar interaction that are present, the more suitable the highly porous solid is for the purposes of the present invention. The surface is determined by argon adsorption at −196° C. in accordance with the known BET method.

Pyrogenic, non-porous silicon dioxide having a BET-surface of from 50 to 500 m²/g and preferably from 400 to 500 m²/g may also be used as the solid for the purposes of the invention. In this case, too, the larger the surface and the greater the number of adsorption centres having a predominantly polar aftereffect that are present, the more suitable the substance is.

Active carbon is preferably used in accordance with the present invention. Suitable active carbons are commercially available. Active carbons are highly porous substances having specific surfaces of from 600 to 1000 m²/g. They show good adsorption properties both for polar substances, such as water and alcohols, and also for apolar substances, such as benzene or alkanes, i.e. on the whole the active carbons have non-specific adsorption properties.

Any controlled modification of the adsorption surface, preferably the surface of the active carbon, may be preceded by exact characterisation of the surface of the adsorbent or active carbon. The results of this characterisation are the nature, number, energetics and preferred interaction of the adsorption sites of the adsorbent or active carbon surface.

Active carbon contains certain active terminal groups on its inner and outer surface, such as for example —OH, —COOH, —CO₂ and CO-groups, as shown in the following:

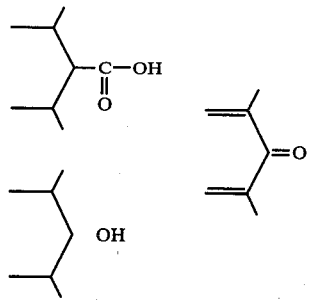

The number and density and type of active terminal groups which the adsorption sites form on the surface of the active carbon may be varied, for example in vacuo, as shown in the following equation:

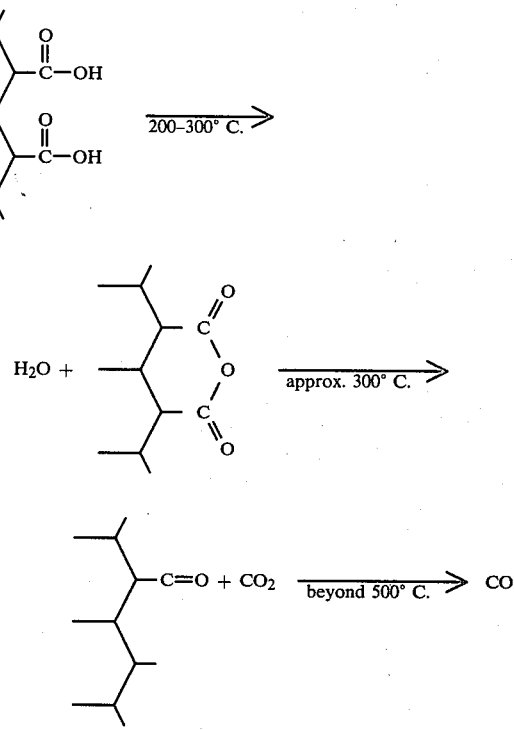

The variation of the active terminal groups depends inter alia on the type of starting carbon used, on the terminal groups present, on the intensity of the vacuum and on the temperature. Zeolites, silicon dioxide and aluminium oxide contain as adsorption sites on their surfaces OH-groups which show a basic or acid or both basic and acid reaction or which, as in the case of silicon dioxide, show a neutral reaction. These groups may occur in pairs or singly.

The variation of the active terminal groups is important to any coupling-on of catalyst molecules and to their surface density variation.

The surface of the porous solid is characterised by adsorption methods, desorption methods and by photoelectron-spectroscopic methods. The results obtained include the nature, number, distribution and energetics of the adsorption sites on the surface of the porous solid [(cf. G. Hellwig, Farbe and Lack 81, page 705 (1975); G. Hellwig ibid. 82, page 582 (1976); G. Hellwig, Blucher Manual, July 1976, page 8 (1976)].

In highly simplified terms, the adsorption sites may be divided up into two groups, namely into those which interact primarily with polar molecules and those which interact primarily with apolar molecules. Difficulties will always arise when certain polar substances have to be adsorptively removed from polar carrier gas mixtures or liquids and when apolar substances have to be adsorptively removed from apolar carrier gas mixtures or liquids. In this case, the polar carrier gas or solvent molecules and the apolar carrier gas or solvent molecules will always occupy the corresponding adsorption sites of the porous solid and, hence, will rapidly render the adsorbent incapable of performing its actual function.

Where filters are used in the region of the intestine and at the outlet thereof, polar substances have to be removed from polar solvents and polar carrier gas mixtures. In order to increase the effective life of a filter for the above-described function, the characterised adsorbent surface is modified with suitable metal salts in a suitable surface density. As a result, the surface of the adsorbent becomes covered with metals. Covering of the adsorbent surface has to be carried out in a specific manner. Controlled pretreatment of the adsorbent creates a certain number of available adsorption sites on the surface of the adsorbent, of which a certain number subsequently becomes covered with metal salts.

The choice of the metal salts depends upon the physical properties of the substances to be removed. The metal salts are determined in a test. The surface density depends upon the size and dipole moment of the substances to be removed.

According to the invention, the adsorbent surfaces and in particular the active carbon surfaces are covered with metals in a suitable surface density.

Aluminium, zinc, chromium or iron may be used as the metals. Aluminium, zinc and chromium are particularly preferred.

The adsorbent surface and particularly the active carbon surface is covered with the metal in a quantity of from 0.1 to 5% by weight, based on 1 g of adsorbent having a specific surface of 1000 m$^2$/g. The metal is preferably applied in a quantity of from 0.1 to 3% by weight and most preferably in a quantity of from 0.2 to 2.0% by weight. However, coverings in excess of 5% are also possible.

Preferred covering concentrations are in the range from 0.15 to 2.5% by weight for aluminium, in the range from 0.25 to 3.5% by weight for zinc and in the range from 0.3 to 5.0% by weight for chromium. Active carbon covered with the abovementioned metals, aluminium, zinc and chromium, in the concentration ranges indicated is used with particular preference as the adsorbent.

The covering of the metals is expressed in percent by weight, based on the adsorbent having a specific surface of 1000 m$^2$/g. This means that the covering of the metals depends upon the surface and that half the percentages by weight quoted above is required for example for covering a porous solid having a surface of only 500 m$^2$/g, whereas three halves of the abovementioned percentage by weight of metals are required for covering a solid having a surface of for example 1500 m$^2$/g.

In general, covering of the adsorbent, particularly the carbon, is carried out by treating the pretreated adsorbent with an aqueous solution of a water-soluble salt of the metal to be applied or, where the salts used are insoluble in water, in a suitable solution in an organic solvent.

The salts used may be for example chlorides, chromates, titanates, etc. It is preferred to used water-soluble salts, for example zinc chloride or chromium trichloride or iron (III) chloride. If the salts, such as aluminium trichloride for example, are insoluble in water, anhydrous alcohols, such as ethanol for example, may be used as the solvent.

Tests have shown that, in the case of AlCl$_3$, a quantity of 111 mg of AlCl$_3$/g of active carbon represents the most favourable covering for adsorbing thiols. This means that, on a statistical average, every tenth adsorption site is occupied by an Al-atom. Latest measurements have shown that a quantity of only 11 mg of AlCl$_3$/g of active carbon is sufficient to produce a comparable effect in the destruction of methane thiols. The destruction of thioacetic acid or carbon disulphide requires from 13 to 130 mg of ZnCl$_2$ or from 15 to 150 mg of CrCl$_3$ per g of active carbon.

The chlorides of zinc and chromium are soluble in water. Aluminium trichloride is dissolved in anhydrous solvents, for example alcohols. After the temperature-vacuum treatment, the solution is directly added to the adsorbent stirred in vacuo, preferably to the carbon, by a special liquid feed system. The pressure prevailing in the reaction vessel falls to around 40 bars. The adsorbents which are now under solvent vapour, for example water vapour, remain in the reaction vessel until they have cooled, but at least for 1 hour and preferably for 4 hours. The reaction vessel is then vented, after which the water and any solvent present are poured off. The product obtained is dried in a drying cabinet. The adsorbent now covered with metal is ready for use.

According to the invention, it is also possible to use mixtures of adsorbents covered with different metals. In one preferred embodiment, a mixture of different active carbons covered with aluminium, zinc and chromium is used.

To test the highly specific adsorbent according to the invention, a number of active carbons with a high proportion of adsorption sites having a predominantly polar interaction are covered with different catalysts. Thus, three quantities of 10 g of active carbon of the Norit-Azo type are covered with the chlorides of aluminium, chromium, iron and zinc. The adsorption capacity of this modified active carbon for methane thiol (CH$_3$SH), ethane thiol (C$_2$H$_5$SH), thioacetic acid (CH$_3$COSH) and carbon disulphide (CS$_2$) was tested in the presence of water, CO$_2$ and methane.

A model intestinal gas was used as the adsorptive. It consisted of a carbon dioxide carrier gas saturated with water and the sulfur compound. The transport velocity $V_T$ of the carbon dilsulfide to be filtered varied from 0.17 mm/sec. to 1.8 ml/sec.

An apparatus was constructed for this purpose, comprising—in a vacuum container—an electronic microbalance, a calorimeter and a mass spectrometer. The model intestinal gas (composition as indicated above) flowing through the filter of modified active carbon is let into the measuring apparatus through a metering valve. FIG. 1 diagrammatically illustrates the construction of the measuring apparatus for a gas mixture of CO$_2$, H$_2$O and CS$_2$ or CH$_2$SH, C$_2$H$_5$SH and CH$_3$COSH.

At a constant temperature of 37° C., the carbon dioxide gas flowing at a constant rate is saturated first with H$_2$O and then with CS$_2$ or CH$_3$SH, C$_2$H$_5$SH and CH$_3$COSH. The model intestinal gas thus formed flows through the carbon filter to be tested and enters a container in filtered form. Adsorption properties, such as the quantity adsorbed, the adsorption energy released and the adsorption energetics as well as the quantities of CS$_2$ or CH$_3$SH, C$_2$H$_5$SH and CH$_3$COSH filtered are simultaneously measured on the same carbon in the above-mentioned container. Parallel with the measurements, the composition of the model gas is determined by a mass spectrometer so that the filter effect throughout the entire filtration process up to break-through and also thereafter is known.

It follows from these tests that the active carbon covered with metals shows a high adsorption capacity for intestinal gases and that, of the metal salts tested, zinc chloride gives the best results. 1 g of carbon covered with the above metals destroys 2 to 3 ml of CH$_3$SH, C$_2$H$_5$SH, CH$_3$COSH and CS$_2$.

Further tests have shown that the other metal-covered adsorbents mentioned above show equally good effects.

It was also found that a different, specially pretreated adsorbent was required for each of the gases to be removed (methane thiol, ethane thiol, thioacetic acid and carbon disulfide). Aluminium and chromium proved to be the most suitable for methane and ethane thiol, respectively, whereas zinc proved to be the most suitable for thioacetic acid and chromium for carbon disulfide. It follows from this that the most effective colostomy filter contains a mixture of three differently modified adsorbents, preferably carbons. According to the invention, therefore, it is preferred to use mixtures of adsorbents, particularly active carbons, coated with different metals.

According to the invention, it is preferred to use as adsorbent a mixture containing from 0 to 50%, preferably from 20 to 40% and, most preferably, 33.33% of adsorbent, particularly active carbon, covered with from 0.1 to 5 and preferably with from 0.15 to 2.5% by weight of Al; from 0 to 50%, preferably from 20 to 40% and, most preferably, 33.33% of adsorbent, preferably active carbon, covered with from 0.1 to 5% and preferably with from 0.25 to 3.5% of zinc; and from 0 to 50%, preferably from 20 to 40% and, most preferably, 33.33% of adsorbent, preferably active carbon, covered with from 0.1 to 5% and preferably with from 0.3 to 5% of chromium. It has surprisingly been found that from 0.5 to 3 g of a mixture such as this is effective for at least 12 hours in adsorbing foul-smelling intestinal gases.

The adsorbent according to the invention as described in the foregoing is introduced into a cylindrical filter cartridge or pad-like bag which is in turn introduced into the colostomy bag.

The invention is illustrated by the following Examples.

EXAMPLE 1

100 g of active carbon are washed with stirring for 30 minutes in 3300 ml of demineralised water. The supernatant suspension is then decanted off and the carbon introduced into a heatable and coolable vacuum container of fine steel. Any extraneous substances which are still adsorbed on the carbon are desorbed while a pressure of up to 10$^{-6}$ bar is established in the container and its contents heated to 150° C.

1.3 g of zinc chloride (p.a.) are dissolved in 300 ml of distilled water. The solution is added with vigorous stirring to the carbon cooled to 100° C. at 10$^{-5}$ bar using a special vacuum feed pipe. A pressure of 40 Torr is immediately obtained inside the container. The carbon is left standing for about 4 hours, after which the container is vented and the carbon is dried in a normal drying cabinet.

EXAMPLE 2

50 g of active carbon are washed for 60 minutes in 200 ml of demineralised water at room temperature in an ultrasonic bath (acoustic power 1 kW at 33 kHz).

The liquid is decanted off from the ultrasonic bath and the washed carbon is introduced into a reaction vessel of steel. The reaction vessel is heated for 30 minutes to 200° C. At the same time, the pressure is reduced to 10$^{-6}$ bar. The extraneous substances adsorbed are removed over a period of 30 to 120 minutes at 10$^{-6}$ bar.

0.55 g of aluminium trichloride are separately dissolved in 200 ml of pure anhydrous ethanol. This solution is added to the carbon cooled to 120° C. with vigorous stirring under a pressure of 10$^{-6}$ bar. The carbon is stirred for another 2 hours, after which the reaction vessel is vented and the carbon is dried in a standard drying cabinet.

EXAMPLE 3

200 g of active carbon are washed with stirring for 60 minutes in 4000 ml of demineralised water at room temperature. The supernatant suspension is then decanted off, after which the carbon is heated for 2 hours at 220° C./10$^{-6}$ bar to desorb any extraneous substances still adsorbed thereon.

1.5 g of chromium trichloride are separately dissolved in 300 ml of twice-distilled water. The solution is added with vigorous stirring to the carbon cooled to 80° C. under a pressure of 10$^{-6}$ bar. The carbon is stirred for another hour, after which the flask is vented and the carbon is dried in vacuo.

EXAMPLE 4

100 g of active carbon powder (Chemviron Sc XII, 6×12, specific surface approximately 1000 m$^2$/g, with approximately 5×10$^{14}$ adsorption sites/cm$^2$ having a predominantly polar interaction and with a heat of adsorption against water of 20.2 kJ/mole) are washed for 30 minutes in 500 cc of demineralised water in an ultrasonic washer (power 1 kW at 30 kHz) and thus freed from coarse impurities and fine particles (dusts). The carbon is air-dried.

The dry carbon is stirred for 30 minutes in an evacuable container at a temperature of 150° C. and under a pressure of from 10$^{-1}$ to 10$^{-3}$ mbar. After the temperature has been reduced from 150° to 100° C., 250 ml of an FeCl$_3$-solution containing 1.5 g of FeCl$_3$ in 250 ml of twice-distilled water are added with stirring to the carbon in the evacuated vessel.

The mixture of carbon and salt solution is stirred in the vessel for about 30 minutes until the temperature has fallen to around 40° C. The liquid phase is then filtered off. The modified active carbon left behind is then ultrasonically washed in 500 ml water baths which have to be repeatedly changed (up to 3 times) until the carbon no longer releases any metal into the aqueous phase (detection limit 0.5 ppm).

The carbon is then air-dried. The carbon retained its grain-size distribution throughout the entire process.

EXAMPLE 5

100 g of active carbon powder (Chemviron Sc XII, 6×12, specific surface approximately 1000 m²/g, with approximately $5 \times 10^{14}$ adsorption sites/cm² having a predominantly polar interaction and with a heat of adsorption against water of 20.2 kJ/mole) are washed for 30 minutes in 500 cc of demineralised water in an ultrasonic washed (powder 1 kW at 30 kHz) and are thus freed from coarse impurities and fine particles. The carbon is then air-dried.

The dry carbon is then stirred for 30 minutes in an evacuable vessel at a temperature of 300° C. and under a pressure of from $10^{-1}$ to $10^{-3}$ mbar. After the temperature has been lowered to 100° C., 250 ml of a $ZnNO_3$-solution containing 1.3 g of $ZnNO_3$ in 250 ml of twice-distilled water are added with stirring to the evacuated carbon-containing vessel. The procedure is then as described in Example 4.

EXAMPLE 6

Quantities of 33.33 g of the carbons obtained in Examples 1, 2 and 3 are accurately weighed off on an analytical balance. The carbons are thoroughly mixed in a mortar and subsequently introduced into cartridges in quantities of 1 g. 100 cartridges are obtained and are introduced into colostomy bags, adsorbing all foul-smelling intestinal gases over a period of more than 12 hours.

We claim:

1. A process for the adsorption and catalytic decomposition of foul-smelling intestinal gases, wherein the intestinal gases are passed through a highly specific adsorbent which, out of a mixture of water vapour, methanol, carbon monoxide and carbon dioxide and various sulfur-containing gases catalytically decomposes and adsorbs only the sulfur compounds, the highly specific adsorbent comprising an inert, highly porous solid having a specific surface according to BET of from 900 to 1800 m²/g, as determined by argon adsorption at −196° C., or pyrogenic silicon dioxide having a specific surface according to BET of from 50 to 500 m²/g, as determined by argon adsorption at −196° C., the surface of the solids being covered with from 0.1 to 5% by weight of aluminium, zinc, chromium or iron, based on the weight of the solid having a specific surface of 1000 m²/g.

2. A process as claimed in claim 1 in which the inert highly porous solid is active carbon, a zeolite or a metal oxide.

3. A process as claimed in claim 2 in which the inert highly porous solid is aluminium oxide or silicon oxide.

4. A process as claimed in claim 1 or 2 characterised in that the highly specific adsorbent comprises highly porous active carbon having a specific surface according to BET of from 1000 to 1800 m²/g, as determined by argon adsorption at −196° C., of which the surface is covered with from 0.1 to 5% by weight of aluminium, zinc, chromium or iron, based on the weight of the active carbon having a specific surface of 1000 m²/g, or a mixture of active carbons of this type.

5. A process as claimed in claims 1, 2 or 3 in which the surface of the solids is covered with from 0.1 to 5% by weight of aluminum or chromium, based on the weight of the solid having a specific surface of 1000 m²/g.

6. A process as claimed in claims 1, 2 or 3 in which a mixture of absorbents is employed, the mixture comprising solids covered with aluminium, solids covered with zinc, and solids covered with chromium.

* * * * *